US006862571B2

(12) United States Patent
Martin et al.

(10) Patent No.: US 6,862,571 B2
(45) Date of Patent: Mar. 1, 2005

(54) CREDENTIALER/MEDICAL MALPRACTICE INSURANCE COLLABORATION

(75) Inventors: David A. Martin, Bentleyville, OH (US); David R. Montgomery, Hudson, OH (US)

(73) Assignee: The Premium Group, Inc., Cleveland, OH (US)

( * ) Notice: Subject to any disclaimer, the term of this patent is extended or adjusted under 35 U.S.C. 154(b) by 12 days.

(21) Appl. No.: 09/339,479

(22) Filed: Jun. 24, 1999

(65) Prior Publication Data

US 2002/0087354 A1 Jul. 4, 2002

(51) Int. Cl.$^7$ .............................................. G06F 17/60
(52) U.S. Cl. ............................................................ 705/4
(58) Field of Search .............................. 705/1, 2, 3, 4; 283/54

(56) References Cited

U.S. PATENT DOCUMENTS

| | | | | | |
|---|---|---|---|---|---|
| 4,831,526 A | * | 5/1989 | Luchs et al. | ................ | 705/4 |
| 4,858,121 A | * | 8/1989 | Barber et al. | ................ | 705/2 |
| 5,070,452 A | * | 12/1991 | Doyle, Jr. et al. | .......... | 705/2 |
| 5,272,623 A | * | 12/1993 | Grubb et al. | ................ | 717/1 |
| 5,640,501 A | * | 6/1997 | Turpin | .................... | 707/507 |
| 5,664,109 A | * | 9/1997 | Johnson et al. | ............ | 705/2 |
| 6,035,276 A | * | 3/2000 | Newman et al. | ............ | 705/2 |
| 6,189,029 B1 | * | 2/2001 | Fuerst | .................... | 709/217 |

FOREIGN PATENT DOCUMENTS

GB 2231420 A * 11/1990 ........... G06F/15/21

OTHER PUBLICATIONS

The Premium Group, Inc. web page. http://www.premiumgroupinc.com/services.html. Downloaded on Mar. 5, 2001.*
"Sweetwater Health Enterprises Receives NCQA Certification, Releases Network Management Software Application," PR Newswire. Sep. 26, 1996. p. 1–2.*

"CompHealth Credentialing Services Certified by the National Committee for Quality Assurance," PR Newswire. Feb. 22, 2001. p. 1–2.*

"Docsbackoffice.com, Inc. Announces CTO Relationship as Part of A Strategic Agreement with Conversion Services International to Outsource its Support, Web Site and Software Projects," Business Wire. Mar. 14, 2000. p. 1–2.*

Turner, Missy. "Bexar Medical Society Taking Credentialing Unit National," San Antonio Business Journal. Feb. 26, 1999. p. 1–2.*

Jaklevic, Starting your own PPM, Apr. 1997, Modern Healthcare, p. 42.*

The Managed care Group—Medical Management—Credentialing.

Federal Credentialing Program.

Industry's First Online Credentialing Service Saves Weeks of Processing Time.

* cited by examiner

Primary Examiner—Joseph Thomas
Assistant Examiner—Christopher L. Gilligan
(74) Attorney, Agent, or Firm—Brouse McDowell; Roger D. Emerson; Daniel A. Thomson

(57) ABSTRACT

An inventive process is disclosed for linking credentialing information with a medical malpractice insurance application. The credentialing information is automatically transferred from the credentialing questionnaire to an insurance application, and this credentialing information is then used to generate a medical malpractice insurance policy. The medical malpractice insurance policy is a two year policy, in order to coincide with the required re-credentialing of the healthcare provider. The inventive process also includes linking an information database, not created for insurance purposes, with an insurance application.

17 Claims, No Drawings

CREDENTIALER/MEDICAL MALPRACTICE INSURANCE COLLABORATION

BACKGROUND OF THE INVENTION

1. Field of Invention

This invention pertains to the art of processes for linking an information database with an insurance application, and more particularly to the process of linking credentialing information with a medical malpractice insurance application.

2. Description of the Related Art

It is well known that regulatory agencies in the United States require health professionals to have their credentials verified every two years. Verification is a time consuming process that typically includes the assembly of various documents, including proof of the physician's license, a valid Drug Enforcement Agency certificate, proof of completion of medical school, proof of board certification, proof of appropriate work history, etc. Thus, the verification process often takes many days and sometimes weeks to complete. Unfortunately, this time consuming process is the only known way that the regulatory agencies can ensure the public that it is receiving care from a qualified medical professional.

It is also well known that the National Committee for Quality Assurance (NCQA) sets the standard for credentialing in managed care organizations. Defined as "the process by which a managed care organization authorizes, contracts, or employs, practitioners, who are licensed to practice independently, to provide services to its members," credentialing simply means making sure that a practitioner is qualified to render care to patients.

Although there is likely to be some variation on the specific criteria used, the basic elements required in establishing proper credentialing information for a physician are likely to include the following: a valid and current license, clinical privileges in a hospital, valid Drug Enforcement Agency (DEA) or Controlled Dangerous Substance certificate (CDS), appropriate education and training (i.e. graduation from an approved medical school and completion of an appropriate residency or specialty program), board certification, appropriate work history, malpractice insurance, and a history of any liability claims. Managed care organizations also credential nonphysician practitioners, such as dentists, chiropractors, and podiatrists. The primary differences between physician and non-physician practitioners for purposes of credentialing, lie in the requirements, and therefore, in the verification of select data. For example, chiropractors are not board certified and do not require DEA or CDS certificates.

Credentialing is a necessary and critical step in securing qualified practitioners to render and manage the care of managed care organization subscribers or members. The managed care organizations oftentimes delegate certain activities in the credentialing process. A Credentials Verification Organization (CVO), which may be certified by NCQA, will verify a practitioner's credentials for a set price. Contracting with a NCQA-certified CVO exempts the hospital, healthcare entity, or managed care organization from the due diligence oversight requirements, specified by NCQA and the Joint Commission for Accreditation of Healthcare Organizations (JCAHO), for all the verification services. By contracting out the necessary credentialing to a NCQA-certrified CVO, the managed care organizations have met their due diligence requirements.

CompHealth, a licensed CVO in the United States, has developed a new web-based credentialing service, moving as much of the process online as possible. One of the keys to the credentialing service is an Internet application called Apply.net. Medical professionals can use the Apply.net application to submit their information to CompHealth via the Internet. However, there is currently in the art no known connection between the credentialing services, the credentialing information, and the insurance industry.

The Federal government has attempted to alleviate some of the problems of credential sharing among separate government entities. The Federal Credentialing Program was created to attempt to electronically link credentialing databases among the federal agencies and departments. However, this credentialing information sharing is limited to the federal government and does not involve the insurance industry.

The present invention provides a process for quickly and efficiently linking credentialing information with a medical malpractice insurance policy. Difficulties inherent in the related art are therefore overcome in a way that is simple and efficient while providing better and more advantageous results.

SUMMARY OF THE INVENTION

In accordance with one aspect of the current invention, the credentialing information is automatically transferred to an insurance application.

In accordance with another aspect of the present invention, at least one medical malpractice insurance premium quote can be generated without the physician having to fill out an application.

Yet another aspect of the current invention includes generating a two year medical malpractice insurance policy in order to coincide with the required re-credentialing of the physician.

In accordance with still another aspect of the current invention, the process includes means for generating the information database for any non-insurance purpose, means for forwarding at least a portion of the information from the information database to an insurance participant, means for generating an insurance premium quote, and means for transferring the at least a portion of the information from the information database to an insurance application.

In accordance with another aspect of the current invention, the process includes a means for providing a questionnaire for gathering information for the database, means for inserting a means for obtaining a customer's permission for release of the information to the insurance participant into the questionnaire, means for inserting at least one more question into the questionnaire, the at least one more question for gathering further information related to a particular insurance product, and means for forwarding all of the questionnaires with an affirmative response to the first question to the insurance participant.

One advantage of the present invention is that the physician will not have to fill out a separate application form for medical malpractice insurance.

Another advantage of the present invention is that the medical malpractice insurance policy is of a duration that corresponds to the recredentialing process, thus eliminating the long term need for physicians to recomplete insurance applications or insurance renewal applications.

Yet another advantage of the current invention is that the entire process can be automated, thereby, creating a quick and efficient process.

Still another advantage of the current invention is that the process increases competition among malpractice insurers by giving them easier access to potential insureds.

One more advantage of the current invention is that the process will drive down the healthcare provider's processing costs, thereby lowering costs of one of physicians' largest line item expenses, thereby lowering the costs of healthcare to consumers.

Still other benefits and advantages of the invention will become apparent to those skilled in the art to which it pertains upon a reading and understanding of the following detailed specification.

DESCRIPTION OF THE PREFERRED EMBODIMENT

The inventive process is designed to link credentialing information with a medical malpractice insurance application. The credentialing information, which the regulatory agencies require of health professionals, can be compiled for each physician by a credentials verification organization (CVO). The credentialing information, however, can be gathered by any entity licensed to do so. The CVO typically obtains and/or verifies required information about each physician, including, a valid and current license, clinical privileges at a hospital, valid DEA or CDS certificates, appropriate education and training (i.e., graduation from an approved medical school and completion of an appropriate residency or specialty program), board certification, appropriate work history, malpractice insurance, and a history of liability claims. This information is used by healthcare entities to ensure the public that it is receiving adequate care from a qualified medical professional. What is to be especially noted is that the information gathered by the CVO is virtually identical to the information required to underwrite a medical malpractice insurance policy.

The inventive process begins by having the CVO include means for obtaining the physician's permission for release of the credentialing information to the medical malpractice insurance participant. This means for obtaining the physician's permission could be in the form of a question added to the questionnaire, requesting the physician's permission. An example of what the question might be is, "May we release this information for the purpose of obtaining competitive malpractice insurance quotes for you?" The means for obtaining permission could also include a statement above the signature line stating that by signing the questionnaire the doctor is giving the CVO permission to release the information to the medical malpractice insurance participant. All of the credentialing questionnaires in which such permission is granted are then automatically forwarded by the CVO to the medical malpractice insurance participant. What is meant by the term "medical malpractice insurance participant" is any one, or more, of the following: insurance companies, brokers, agents, third party administrators, risk bearers, claims managers, risk managers, insurance marketers, and the like.

Using the credentialing information, at least one insurance premium quote is generated for the medical malpractice insurance policy. The medical malpractice insurance participant can provide multiple quotes from various insurance companies to the physician. The insurance participant then contacts the physician with the premium quotes and policy terms and conditions. By "quote" it is meant either a non-binding or binding quote of the cost of the insurance policy premium.

If the physician orders the medical malpractice insurance, the credentialing information is transferred from the credentialing questionnaire to a medical malpractice insurance application. An application for medical malpractice insurance is then generated by a computer for the physician.

The insurance participant then delivers the completed application to the physician for the physician's review and approval.

Once the medical malpractice insurance policy has been approved by the physician, a two year policy is generated by the insurance participant. This two year policy coincides with the required re-credentialing procedure for the physician. The physician will no longer be required to fill out a new application for medical malpractice insurance each time the medical malpractice policy comes up for renewal. Each time the re-credentialing is done, which, in the preferred embodiment, occurs every two years, the updated credentialing information can then be sent again to the insurance participant, and the medical malpractice insurance policy can be renewed with expediency and efficiency.

The two year medical malpractice insurance policy is a preferred embodiment of the invention, and is not intended to limit the invention in any way. The current inventive process also encompasses any length of policy term that coincides with the re-credentialing process. For example, if the re-credentialing occurs every three years, instead of every two years, a three year medical malpractice insurance policy can be issued.

Also, the information on the medical malpractice insurance application, since it is almost identical to the credentialing information, can be transferred back to a credentialing questionnaire for any subsequent health organizations that require credentialing of the subject physician. The medical malpractice insurance participant can transfer this information, and send copies of the credentialing questionnaires to the various health organizations, thereby saving the physician a great deal of time and effort. The physician will no longer be required to fill out multiple credentialing questionnaires for multiple health organizations. In the past, a physician had to fill out a credentialing questionnaire for each and every health organization from which they desired approval. With the inventive process, the physician need only fill out one credentialing questionnaire, and from that, the process transfers the information to a medical malpractice insurance application. From the insurance application, the credentialing information can be transferred to multiple questionnaires to send out to multiple health organizations. All that the physician needs to do is to contact the medical malpractice insurance participant and request that the insurance participant complete a credentialing application for whichever health organization the physician wishes. The medical malpractice insurance participant can then transfer the information from the insurance application to the credentialing questionnaire and provide the completed questionnaire to the physician. The physician then reviews the credentialing questionnaire, signs it, and submits it to the credentialing entity, or health organization. The inventive process encompasses all of the subsequent applications and questionnaires that the physician would need for any subsequent health organizations that require the credentialing information.

If a physician has already obtained medical malpractice insurance coverage, the medical malpractice insurance participant will have all, or most, of the information necessary for the credentialing process. This invention also encompasses the initial step of the process being the medical malpractice participant transferring the information from the medical malpractice insurance application to the credentialing questionnaire. In this manner, the credentialing process can be efficiently and quickly completed even after the physician has a medical malpractice insurance policy.

In either of the situations where the information is going from the insurance application to the credentialing questionnaire, or vice versa, it is possible that some of the questions will not match up. If one of the questions on either the credentialing questionnaire or the insurance application is left blank due to the questions not matching up, these questions will be highlighted, and when the physician receives the application or questionnaire, the physician will fill in the highlighted blank spaces.

In the preferred embodiment, the inventive process occurs automatically via electronic transmission and computer data manipulation. The required computer hardware, and the necessary computer code, would be obvious to one skilled in the computer art.

However, this invention is not limited to the preferred embodiment, and can be accomplished without the use of computers or electronic means. The methods of transferring information manually, or by way of a hybrid combination of manual and electronic transference, are both encompassed by this invention. In the manual, or hybrid of manual and electronic, transference embodiments, the steps taken to link the insurance application with the credentialing information are identical to the steps taken in the preferred embodiment, and those steps are incorporated herein by reference.

The present invention is also not limited to the medical malpractice field, but includes the entire range of insurance participants. The present invention can be used to link any information database, not created for insurance purposes, to any type of insurance application. The only information databases not encompassed within this invention would be databases created for the purpose of filling out an insurance application, or for the purpose of obtaining any type of insurance. An example of the type of information database not encompassed within this invention would be an Internet insurance application form. However, any other information database, not created for insurance purposes, can be linked by this inventive process to an insurance application. The means by which this information is linked with the insurance application is identical to the process described in the medical malpractice insurance process, and the steps of the process are incorporated herein by reference. However, when linking the information to other forms of insurance, further questions may need to be added in order to gather further, necessary information. An example of some further questions, necessary for life insurance, would be whether someone is a smoker or a nonsmoker.

The types of insurance applications that can be linked can include, but are not limited to, the following: life insurance, automobile insurance, medical malpractice insurance, legal malpractice insurance, professional liability insurance, health insurance, disability insurance, renter's insurance, homeowner's insurance, flood insurance, fire insurance, hurricane insurance, and earthquake insurance, or any other line of insurance.

It is to be noted that the invention encompasses the idea that the credentialing organization, the healthcare entity, the insurance participant, etc. can be one entity or separate entities. For example, a hospital that does its own credentialing and provides insurance for its physicians is encompassed within this invention.

In another embodiment of this invention, there is no need for a credentialing questionnaire to be provided. The CVO should have all the data necessary for filling out an insurance application, and all that would be needed would be the physician's permission for use of the information. In this embodiment, the initial step of the process would be transferring the credentialing information from the CVO directly into either an insurance application or an insurance policy.

The invention also encompasses the use of electronic transmission of the information to the physician for the physician's approval. The physician could then send approval for the insurance policy back to the insurance participant. Under this method of the invention, no signature is required by the physician, only the physician's approval of the insurance policy.

The invention has been described with reference to preferred embodiments. Obviously, modifications and alterations will occur to others upon a reading and understanding of this specification. It is intended to include all such modifications and alternations in so far as they come within the scope of the appended claims or the equivalents thereof.

Having thus described the invention, it is now claimed:

1. A process of linking credentialing information with a medical malpractice insurance application, the process comprising the steps of:

providing a questionnaire for use in compiling credentialing information concerning an associated physician to create a first credentialing application, the questionnaire including means for obtaining the physician's permission for release of the credentialing information to an associated medical malpractice insurance participant;

electronically forwarding the information to an associated credentialing entity;

verifying the credentialing information;

electronically forwarding the questionnaire from the credentialing entity the medical malpractice insurance participant if the physician gave permission for release of the credentialing information;

providing the physician with at least one insurance premium quote generated by the medical malpractice insurance participant for use in generating a medical malpractice insurance policy for the physician based at least in part on the credentialing information;

preparing a medical malpractice insurance application for the physician;

electronically transferring at least a portion of the verified credentialing information from the questionnaire to the medical malpractice insurance application;

completing the formation of the medical malpractice insurance application;

delivering the medical malpractice insurance application to the physician for the physician's review and approval;

generating the medical malpractice insurance policy to coincide with subsequent credentialing applications for the physician;

electronically transferring the credentialing information from the medical malpractice insurance policy to the subsequent credentialing application;

generating a subsequent credentialing application; and, sending the subsequent credentialing application to an associated healthcare organization to which the physician must provide the credentialing information.

2. A process of linking credentialing information with a medical malpractice insurance application, the process comprising the steps of:

compiling credentialing information from a credentialing questionnaire regarding an associated healthcare provider;

obtaining the healthcare providers permission for release of the credentialing information to a medical malpractice insurance provider;

electronically forwarding at least a portion of the credentialing information to an associated medical malpractice insurance participant;

electronically transferring the at least a portion of the credentialing information to a medical malpractice insurance application; and, processing the medical malpractice insurance application based on the at least a portion of the credentialing information.

3. The process of claim 2, wherein after forwarding at least a portion of the credentialing information from the credentialing entity to the medical malpractice insurance participant, the process comprises the step of:

providing the healthcare provider with at least one insurance premium quote for a medical malpractice insurance policy generated by the medical malpractice insurance participant.

4. The process of claim 2, wherein the process further comprises the step of:

delivering the medical malpractice insurance application to the healthcare provider for the healthcare provider's review and approval.

5. The process of claim 4, wherein the step of generating an insurance premium quote for a medical malpractice insurance policy comprises the steps of:

quoting the insurance premium to the healthcare provider; and, selling the medical malpractice insurance policy to the healthcare provider.

6. The process of claim 5, wherein the process further comprises the step of:

generating the medical malpractice insurance policy, the policy being a two-year policy, in order to coincide with a required re-credentialing procedure for the healthcare provider.

7. The process of claim 6, wherein the of forwarding the credentialing information to a medical malpractice insurance participant comprises the steps of:

inserting means for obtaining the healthcare providers permission for release of the credentialing information to a medical malpractice insurance provider into the questionnaire, and, electronically forwarding all of the credentialing questionnaires with an affirmative response to the medical malpractice insurance participant.

8. The process of claim 7, wherein the process further comprises the steps of:

generating a second credentialing application;

electronically transferring the credentialing information from the medical malpractice insurance application to the second credentialing application; and, sending the second credentialing application to another health organization to which the physician must provide the credentialing information.

9. The process of claim 8, wherein the process further comprises the step of:

repeating the preceding three steps of claim 8.

10. The process of claim 2, wherein electronically forwarding at least a portion of the credentialing information from the credentialing entity to the medical malpractice insurance participant further comprises the step of:

electronically forwarding at least a portion of verified credentialing information from the credentialing entity to the medical malpractice participant.

11. An apparatus for linking credentialing information with a medical malpractice insurance application, the apparatus comprising:

means for compiling credentialing information regarding an associated healthcare provider from a credentialing questionnaire;

means for electronically forwarding the credentialing information to an associated medical malpractice insurance participant;

means for generating at least one insurance premium quote for a medical malpractice insurance policy; and, means for electronically transferring to credentialing information from the credentialing questionnaire to the medical malpractice insurance application.

12. The apparatus of claim 11, wherein the apparatus further comprises means for generating to medical malpractice insurance policy, the policy being of a duration, in order to coincide with a required re-credentialing procedure for the healthcare provider.

13. The apparatus of claim 11, wherein the means for electronically forwarding the credentialing information to a medical malpractice participant further comprises:

means for electronically forwarding verified credentialing information to a medical malpractice insurance participant.

14. A process for linking credentialing information with a medical malpractice insurance policy, the process comprising the steps of:

providing means for obtaining an associated healthcare provider's permission to release the credentialing information to an associated medical malpractice insurance participant;

receiving permission from the healthcare provider to release the credentialing information;

electronically forwarding at least a portion of the credentialing information from an associated credentialing entity to the medical malpractice insurance participant; and, providing the healthcare provider with at least one insurance premium quote for a medical malpractice insurance policy generated by the medical malpractice insurance participant.

15. The process of claim 14, wherein the process further comprises the steps of:

receiving the healthcare provider's approval of the at least one insurance premium quote; and, creating a medical malpractice insurance policy.

16. The process of claim 15, wherein providing the healthcare provider with at least one insurance premium quote for a medical practice insurance policy generated by the medical malpractice insurance participant comprises the steps of:

providing the healthcare provider with at least one insurance premium quote for a medical malpractice insurance policy generated by the medical malpractice insurance participant; and, electronically transferring the credentialing information to a medical malpractice insurance application.

17. The process of claim 14, wherein electronically forwarding at least a portion of the credentialing information from the credentialing entity to the medical malpractice insurance participant further comprises the step of:

electronically forwarding at least a portion of verified credentialing information from the credentialing entity to the medical malpractice insurance participant.

* * * * *

UNITED STATES PATENT AND TRADEMARK OFFICE
CERTIFICATE OF CORRECTION

PATENT NO. : 6,862,571 B2
DATED : March 1, 2005
INVENTOR(S) : David A. Martin

It is certified that error appears in the above-identified patent and that said Letters Patent is hereby corrected as shown below:

<u>Column 8,</u>
Line 19, "transferring to credentialing" should be -- transferring the credentialing --.
Line 23, "generating to medical" should be -- generating the medical --.

Signed and Sealed this

Eighteenth Day of October, 2005

JON W. DUDAS
*Director of the United States Patent and Trademark Office*